United States Patent [19]

Folkman

[11] 4,314,586

[45] Feb. 9, 1982

[54] DISPOSABLE VALVE

[75] Inventor: Bern D. Folkman, Burbank, Calif.

[73] Assignee: Tronomed International, Inc., Costa Mesa, Calif.

[21] Appl. No.: 163,778

[22] Filed: Jun. 27, 1980

Related U.S. Application Data

[63] Continuation of Ser. No. 937,952, Aug. 30, 1978, abandoned.

[51] Int. Cl.³ .............................................. F16K 5/04
[52] U.S. Cl. .............................. 137/625.47; 251/309; 251/368; 251/DIG. 5
[58] Field of Search ...................... 137/625.19, 625.22, 137/625.32, 625.41, 625.47; 251/309, 310, 312, 368, DIG. 5; 128/205.24, 273, 274

[56] References Cited

U.S. PATENT DOCUMENTS

| | | | |
|---|---|---|---|
| 2,854,027 | 9/1958 | Kaiser et al. | 137/625.47 |
| 3,124,335 | 3/1964 | Mason | 251/309 |
| 3,395,890 | 8/1968 | Eckert | 251/368 |
| 3,678,960 | 7/1972 | Leibinsohn | 251/309 |
| 3,774,604 | 11/1973 | Danielsson | 251/309 |
| 3,780,736 | 12/1973 | Chen | 137/625.47 |
| 3,783,900 | 1/1974 | Waldbillig | 251/309 |
| 3,788,599 | 1/1974 | Cloyd | 251/309 |
| 3,788,602 | 1/1974 | Kitzie | 251/312 |
| 3,957,082 | 5/1976 | Fuson et al. | 128/214 B |
| 4,003,403 | 1/1977 | Nehring | 137/625.47 |
| 4,146,055 | 3/1979 | Ryder et al. | 251/312 |
| 4,147,184 | 4/1979 | Jess | 251/312 |

FOREIGN PATENT DOCUMENTS 833247  4/1960  United Kingdom .

Primary Examiner—Martin P. Schwadron
Assistant Examiner—H. Jay Spiegel
Attorney, Agent, or Firm—Jackson, Jones & Price

[57] ABSTRACT

A low-cost, two-piece medical valve with improved reliability which can be made utilizing a broader range of materials then heretofore possible and capable of manufacture with easily maintainable molding tolerances. These improvements result from the incorporation of a straight cylindrical seal between the valve core and body permitting limited axial movement. The valve is molded in such a manner to create a strong interlock between the valve ports and to eliminate heavy sections of plastic adjacent to the sealing area of the valve.

9 Claims, 8 Drawing Figures

DISPOSABLE VALVE

RELATED APPLICATIONS

This is a continuation application of Ser. No. 937,952 filed on Aug. 30, 1978, now abandoned.

BACKGROUND OF THE INVENTION

1. Field of the Invention

The present invention relates to a medical valve assembly and, more particularly, to a two-piece three-way plastic medical valve assembly.

2. Description of the Prior Art

Disposable plastic valves are used extensively in the medical industry because it guarantees to the patient a product which has never been used and it relieves scarce hospital personnel of cleaning, assembly, and quality control when this can best be done by a manufacturer on a mass production basis. Ideally, the valve must meet exacting requirements such as consistent and uniform function without leakage. It must be made at lowest possible cost. If possible, the valve should be producible from a range of materials suitable to meet the needs of the user; clear plastics for some uses, lowest cost plastics to fill another need, specific plastics compatible for assembly to other equipment to fill still a third need.

Valves presently on the market do not have all of these desirable features. Design and molding specifications limit the range of usable materials and the exacting functional requirements are only achievable at higher than desirable cost.

For example, in valves of the type described herein, there is a core and body tapered so that they can come together to a perfect fit. This fit can only be maintained if the core and body are held tightly for any axial shift will cause the valve to leak. In some valves, there is a mechanical interlock between the core and body which holds the two parts. In other valves, the core is held into the body with a third member, a retaining ring. In order to maintain the core and body positioned as required, very close molding tolerances must be held on diameters and on the axial dimensions of the interlock or retaining ring. This increases cost for when the tolerances are not held as is often the case in high-speed, mass production techniques, the parts must be rejected. The tolerance problem is alleviated partially by making the valve from specific, rigid plastics. The plastics chosen are usually a forced compromise between cost, producibility, and the needs of the user.

A further problem relates to the lubrication of disposable valves. This is an expensive and unsatisfactory manufacturing step. The lubricant is an oil which is usually hand-applied to the core or body immediately before assembly. During subsequent handling and packaging, a small portion of this oil or any excess will run and will often be found on the external male sealing surface (Luer taper). The valve can then not be securely assembled into other equipment creating a significant medical hazard.

SUMMARY OF THE INVENTION

As a part of this invention, I have found that disposable valves work quite satisfactorily when certain lubricants are incorporated into the core plastic material before molding. This is made feasible by essentially eliminating the dependency of the assembly process on material properties. I have further developed a straight-sided, core-to-body fit with limited axial movement and have greatly improved the interlock. Furthermore, these design improvements have eliminated the need for exacting tolerances and have reduced the valve cost.

It is an object of this invention to provide a low-cost, two-piece, easily assembled valve.

It is an object of this invention to provide a valve with improved function and reliability which can be readily molded and held together using easily maintainable tolerances.

It is an object of this invention to provide a valve which can be made in a wide range of materials primarily selected to meet the needs of the user.

It is a further object of this invention to provide an improved method of molding the valve.

Other objects of this invention will become apparent from further description and from the following illustrations in which:

DESCRIPTION OF THE PREFERRED EMBODIMENT

Figure 1:
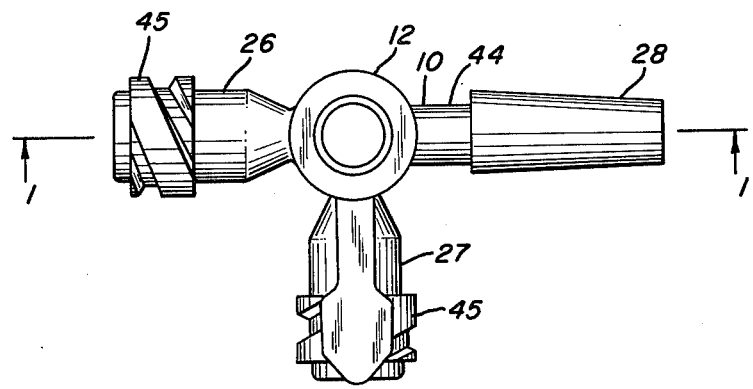
FIG. 1 is a top view of the invention.
Figure 2:
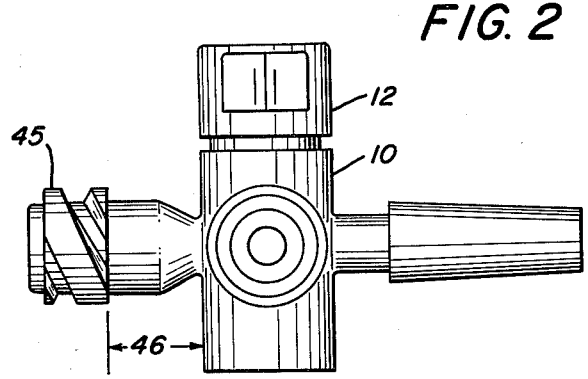
FIG. 2 is an elevational view.
Figure 3:
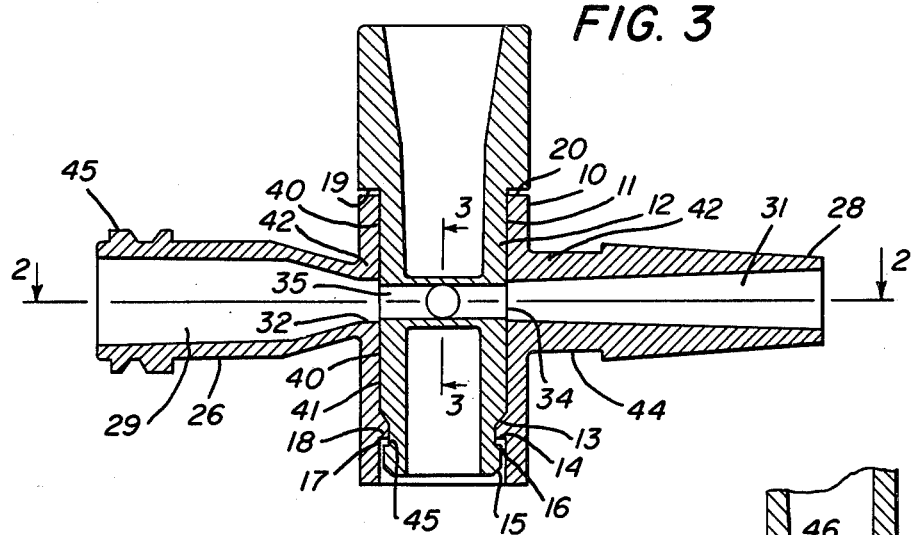
FIG. 3 is an enlarged section view, in elevation, on the line 1—1 of FIG. 1.

The valve of the present invention has a cylindrical body 10 with a straight axial bore 11 passing longitudinally through it as shown in FIGS. 1 through 4. The bore 11 contains a tight-fitting, rotatable core 12. As shown in FIG. 3, the lower portion of the bore tapers inwardly 13 then abruptly widens out again to form a horizontal surface or stop 14.

The core 12 has a tapered lead-in surface 15 which widens out to almost full diameter 16 then abruptly decreases in diameter to form a horizontal matching stop 17. This configuration permits easy assembly of the valve by pushing the lead-in of the core 15 past the taper of body 13 while slightly flexing the body until the stops 14 and 17 have passed each other. At this point, it is no longer possible to remove the core from the body as the stop 14 will not permit passage of stop 17. As shown, the valve may be assembled so a space 18 exists, thus a vertical, axial movement of the core is permitted limited in the upward direction by stops 14 and 17 and in the downward direction by the bottom surface of the core cap or stop 19 hitting the exterior body top surface 20. The ability of the valve to maintain a tight seal is unaffected by axial movement because of the straight sides of bore 11.

Body 10 has three tubular extensions 26, 27 and 28 projecting perpendicular and containing passages 29, 30 and 31, respectively, which are open to the bore of the body through ports 32, 33 and 34, respectively.

Core 12 contains two transverse passages 35 and 36. Passage 35 extends straight through the core whereas passage 36 extends at 90 degrees from passage 35 to the outside of the core.

Ports 32, 33 and 34 are vertically elongated so that passages remain freely open into the core unaffected by the axial movement of the core.

Prevention of sinks in the body and core sealing surfaces 40 and 41 is of great importance to prevent leakage of the valve. Whenever there are heavy sections of plastic, especially where two wall sections come together, such as the volume 42 of the body, there is a tendency during injection molding for there to be less packing of the plastic in the section resulting in shrinkage on cooling, which in turn causes a depression or sink on the surface.

Figure 4:
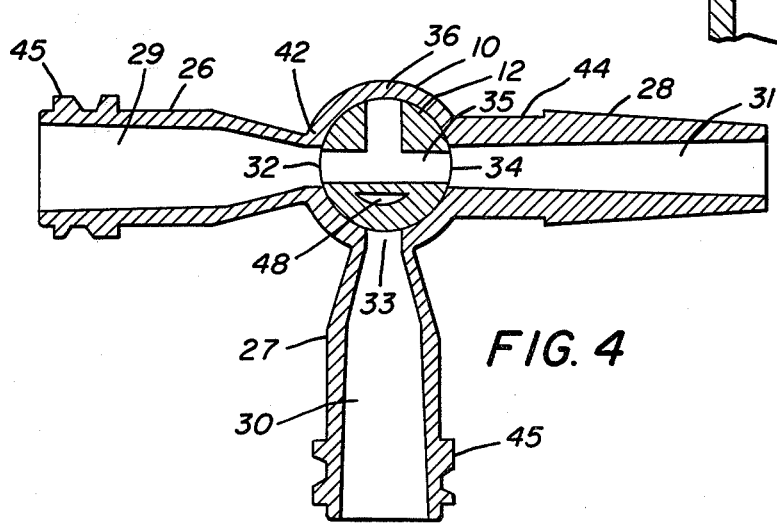
FIG. 4 is a plan view of the valve body and core on the line 2—2 of FIG. 3.

In FIGS. 3 and 4, it can be seen that the walls defining passages 29, 30 and 31 all taper inwardly as they approach ports 32, 33 and 34 in order to maximize the sealing surface 40 of bore 11. Correspondingly, the outer walls of extensions 26 and 27 are also tapered as they enter body 10 so as to minimize thickness of plastic at the wall junction 42 with body 10 and prevent sinking in the sealing surfaces 40. Extension 28 has a notch 44 cut to minimize wall thickness as well as accommodate a snap-fit lock which many users employ to hold mating parts firmly to the taper of extension 28.

Screw-threaded adapters 45 are molded as an integral part of extension 26 and 27. As shown in the drawings, an adequate distance 46 between the inboard end of the adapter 45 and the cylindrical body 10 must be maintained or the effect of the heavy section of plastic may cause distortions in the wall of the body 10 and affect the sealing surface 40.

Figure 5:
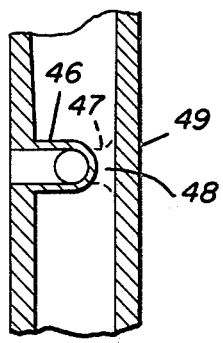
FIG. 5 is an enlarged sectional view of the core passageway section only, on the line 3—3 of FIG. 3.

In the core, there is a particularly severe problem caused by the heavy wall section 48 shown in FIG. 5. In valves currently on the market, an attempt has been made to solve this problem by forming the contour shown by dotted line 47. The results of this are not always successful because there is still a heavy thickness of plastic to cool at section 48 and a sink is found in the sealing surface at 49. We have found that by eliminating section 48 entirely, leaving an open bore, the sinking problem is eliminated.

Figure 6:
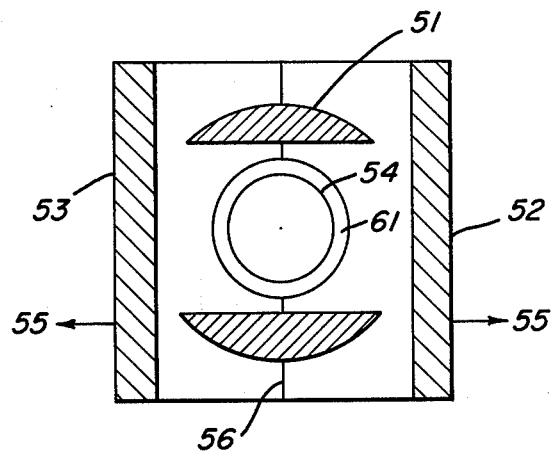
FIG. 6 is a plan view of the core mold on the line 4—4 of FIG. 7.
Figure 7:
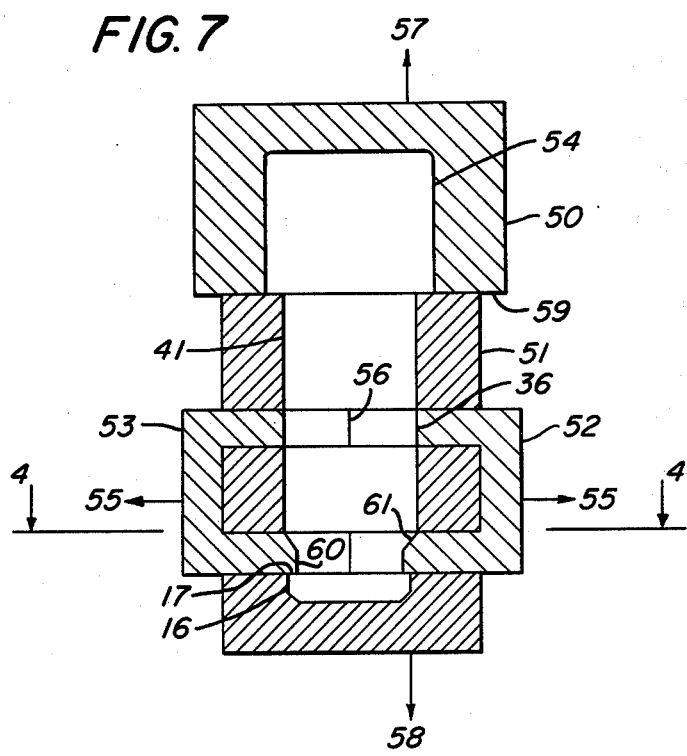
FIG. 7 is a sectional view of the mold, which forms the valve core.
Figure 8:
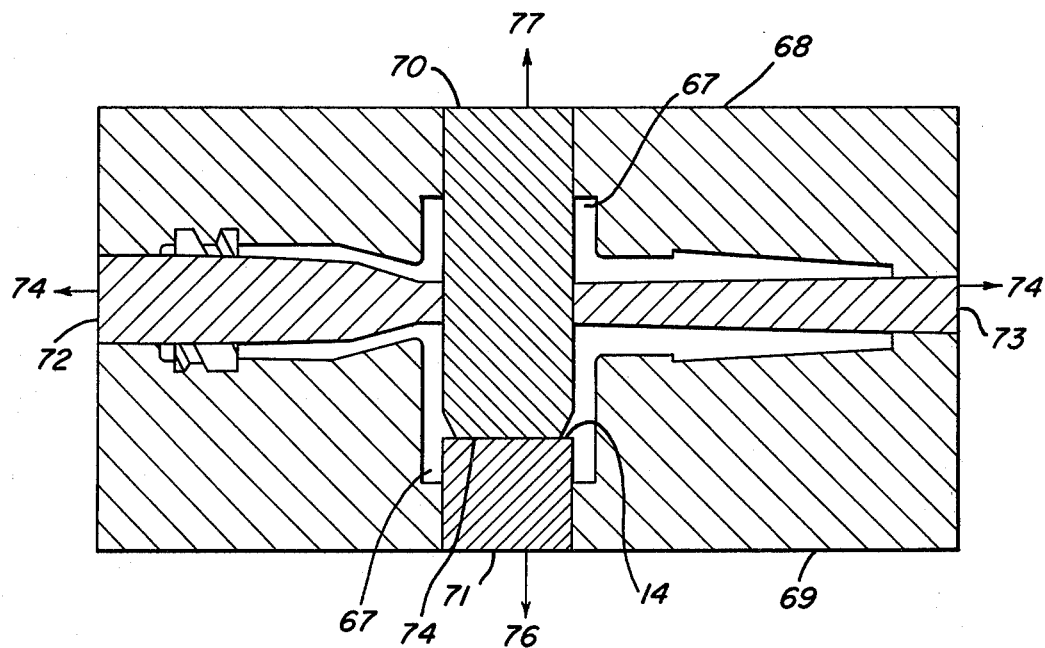
FIG. 8 is a sectional view of the body mold.

FIGS. 6 and 7 depict pertinent sections of the molds used for forming the core and FIG. 8 illustrates the method by which the body is formed. Referring to FIGS. 6 and 7, the core mold consists of blocks of steel 50, 51, 52 and 53 encompassing cavity 54 into which plastic will be injected to form the core. The portion of the mold which forms the hollow internal section of the core is not shown. Undercut surface 17 and the core passage 35 are formed by blocks 52 and 53. The straight sealing surface 41 of the core is formed by block 51 and the head of the core is formed in block 50.

Plastic is injected into cavity 54 and allowed to cool. Blocks 52 and 53 then open by being pulled in the direction of arrow 55. Blocks 52 and 53 open until surfaces 56 have cleared block 51. Then blocks 50 and 51 are free to open parting at surface 59 and moving in the directions 57 and 58, respectively, until the core falls free. By molding in this manner, there is no mold parting line on sealing surface 41, the parting line is on undercut surface 17.

This molding method, just described, is a departure from the conventional means of molding valves. In place of block 52, there is ordinarily a single pin to form the core passage 35. The lower portion of the core mold 51, in order to leave no parting lines on the sealing surface, must pull in the direction 58 past undercut 17.

To accommodate this, the undercut cannot be horizontal, but must be angled usually no less than 45 degrees to the horizontal. Additionally, the size of the undercut as measured by the difference in radius between 16 and 60 is limited in design to about 0.010 inches with relatively soft plastic materials and to about 0.005 inches when molding harder plastics. Tolerances created in the molding process must be added to the design dimension and since the minimum tolerance encountered with commonly used plastics is 0.001 to 0.003 inches, the undercut in hard materials may be as small as 0.002 inches in a percentage of parts. After subsequent assembly of the valve, 0.002 inches undercut is not enough to hold the core securely within the body.

Referring to FIG. 8, the body is formed by a cavity 67 cut into the mold blocks 68 and 69. The internal portions of the body are formed by pins 70, 71, 72 and 73. The undercut portion of the body 14, which will subsequently hold the core in place, is formed at the parting line 74. After cavity 67 has been filled, and the plastic allowed to cool, pins 72 and 73 are pulled from the mold in direction indicated by arrows 74 and 75, respectively. The mold blocks 68 and 69 are now free to open, also moving in counterposition to each other in the direction of arrows 76 and 77, and the completely molded valve body drops free.

The means for molding the valve body is also a departure from conventional methods. Ordinarily, only one pin is used to form the body interior surface replacing pins 70 and 71 and pulling from the top in direction 77. A situation similar to that of the core exists in that to permit passage of the single pin during retraction, undercut surface 14 cannot be horizontal but must be angled. Following the same reasoning as applicable to the core, the molded undercut may be as small as 0.002 inches. It will happen that cores and bodies both with minimal undercuts will be assembled in the same valve. This, together with the fact that the undercut surfaces 14 and 17 are not horizontal but angled, will mean that the valve assembly is very insecure and will be a reject in production. Use of softer or lubricated plastics further aggravates this condition.

It is clear then that the molding technique described herein permits greater molding tolerances and significantly broadens the range of useful valve materials. For instance, among materials which can be used to mold the core, it was found that polypropylene, linear polyethylene, and nylon impregnated with materials such as Teflon, zing stearate, and polyethylene waxes can all be used in the manufacture of a valve which functions satisfactorily without externally applied lubricant. The quantity of incorporated material is only about 2–30%; therefore, the cost is low and the cores can be molded in conventional equipment. Pure Teflon for those users who wish it can also be used for the valve core, even though it is soft.

While the preferred embodiment has been disclosed, various modifications and alternative embodiments of the present invention could be accomplished within the scope of the present invention and accordingly, the present invention should be measured solely from the following claims.

I claim:

1. A disposable plastic valve comprising:
   a body with inlet and outlet extensions and having a substantially straight cylindrical bore of a relatively constant diameter and a tapered portion forming a first stop member extending into the bore;

a valve core rotatably mounted in the body with a cylindrical surface sealingly contacting the bore, the valve core is configured to minimize the quantity of plastic subject to solidification and thereby prevent warpage that could permit leakage of the valve;

conduit means in the valve core capable of fluidly connecting the inlet and outlet extensions;

a second stop member on the valve core of a complimentary configuration to the tapered portion of the first stop member of the body wherein the valve core can be forced past the tapered portion of the body to be permanently secured in an operative position, and a third stop member on the valve core engageable with an exterior top surface on the body, the relative position of the first and second stop members permitting a limited axial sealing movement of the valve core within the body cylindrical bore in one direction and the relative position of the third stop member and the exterior top surface limiting axial sealing movement of the valve core in an opposite direction, the valve core within its range of axial movement still maintaining an operative relationship of the inlet and outlet extensions.

2. The invention of claim 1 wherein the valve consists of only a valve body and a valve core, the valve body having three peripherally spaced ports, the inlet and outlet extensions including respective tubular extensions aligned with and extending from each port and adaptable for connection to fluid conduits, and the second stop member on the valve core is within the valve body while the third stop member on the valve core is external to the valve body.

3. The invention of claim 2 wherein the first stop member has an annular tapered surface adjacent one end of the bore extending into the bore and forming a flat annular stop member.

4. The invention of claim 1 wherein the first stop member has an annular tapered surface extending into the bore and forming a flat annular member.

5. A two-piece, three-way disposable plastic valve comprising:

a valve body having a substantially straight inner cylindrical surface bore with three peripherally spaced ports and an annular tapered surface adjacent one end of the bore extending into the bore and forming a first flat annular stop member;

a respective tubular extension aligned with and extending from each port, at least two of the tubular extensions having a first diameter portion adaptable for connection to a fluid conduit and a second reduced diameter portion adjacent their respective ports to minimize the quantity of plastic adjacent the valve body which is subject to cooling during solidification to prevent sink warpage of the cylindrical bore which could permit leakage of the valve;

a substantially hollow valve core rotatably mounted in the valve body with an outside cylindrical surface sealingly contacting the bore;

conduit means in the valve core capable of fluidly connecting at least two valve body ports;

a second stop member on the valve core of a complimentary configuration to the tapered portion of the valve body wherein the valve core can be forced past the tapered portion of the valve body to be permanently secured in an operative position, the relative alignment of the first and second stop members permitting a limited axial sealing movement of the valve core within the valve body cylindrical bore while still maintaining an operative relationship of the valve body ports with the conduit means.

6. The invention of claim 5 wherein the second stop member on the valve core is within the valve body and a third stop member on the valve core is external to the valve body and engageable with an exterior top surface on the valve body.

7. The invention of claim 6 wherein each tubular extension includes means for attachment of fluid conduits.

8. The invention of claim 5 wherein the valve core comprises two separate materials, a first moldable plastic material impregnated with two percent to thirty percent of a second separate material having a lubricating characteristic.

9. The invention of claim 8 wherein the lubricating material is selected from a group consisting of Teflon, zinc stearate and polyethylene wax.

* * * * *